United States Patent
Grundei et al.

(10) Patent No.: US 7,628,820 B2
(45) Date of Patent: Dec. 8, 2009

(54) SET FOR CREATING AN OFFSET-RESURFACING HIP-JOINT IMPLANT

(75) Inventors: Hans Grundei, Lübeck (DE); Ludger Gerdesmeyer, Kiel (DE)

(73) Assignee: ESKA Implants GmbH & Co. KG, Lübeck (DE)

( * ) Notice: Subject to any disclaimer, the term of this patent is extended or adjusted under 35 U.S.C. 154(b) by 0 days.

(21) Appl. No.: 12/169,720

(22) Filed: Jul. 9, 2008

(65) Prior Publication Data

US 2009/0018666 A1   Jan. 15, 2009

(30) Foreign Application Priority Data

Jul. 9, 2007   (DE) ................ 10 2007 032 583

(51) Int. Cl.
*A61F 2/36* (2006.01)
(52) U.S. Cl. .................. 623/23.12; 623/22.17
(58) Field of Classification Search ........... None
See application file for complete search history.

(56) References Cited

U.S. PATENT DOCUMENTS 4,123,806 A   11/1978   Amstutz et al.

FOREIGN PATENT DOCUMENTS

| DE | 94 02 828 U1 | 7/1994 |
|---|---|---|
| DE | 10218801 B3 | 1/2004 |
| DE | 10 2005 006023 B3 | 8/2006 |
| DE | 102005011361 B4 | 2/2007 |
| EP | 0878176 B1 | 10/2003 |
| EP | 1 872 745 A | 1/2008 |
| WO | 2006/094572 A1 | 9/2006 |
| WO | 2007/066156 A1 | 6/2007 |

*Primary Examiner*—Bruce E Snow
(74) *Attorney, Agent, or Firm*—Panitch Schwarze Belisario & Nadel LLP

(57) ABSTRACT

A set is provided for creating an offset-resurfacing hip-joint implant. The set includes a 1 to 1.5 mm thick metallic acetabulum shell (1) for insertion into the natural acetabulum, from which only cartilage has been removed, a metallic head cap (2) for placement on the natural hip-joint head, from which only cartilage has been removed, and an inlay (3) for insertion into the acetabulum shell (1) as a sliding partner for the head cap (2). The inlay has a material thickness of 2 to 5 mm. The head cap (2) has a wall thickness which increases constantly from a thickness of 2 mm to 6 mm viewed in cross section in the region of the base edge (6) of the head cap, so that an eccentricity is produced in its outer shape.

6 Claims, 3 Drawing Sheets

SET FOR CREATING AN OFFSET-RESURFACING HIP-JOINT IMPLANT

BACKGROUND OF THE INVENTION

The invention relates to a set for creating an offset-resurfacing hip-joint implant. This is understood to be a surface replacement for the natural sliding or articulating surfaces of the acetabulum and the hip-joint head.

So-called cap implants, which are placed over the prepared, natural remaining joint head and which can then be fixed in this position, are being used more and more in recent years. Cap implants comprise a cap, which has an outer shape patterned to the natural joint ball and which can be placed on a (partially) prepared, natural remaining joint head. Such an implant can be created from the so-called set for creating a reinforcement implant according to German Patent DE 102 18 801.

A prerequisite for a stable secondary fixation is stable bone material of the remaining bone. For example, in the already mentioned patent it is proposed to couple a peg to the joint head cap, wherein this peg is set in a corresponding milled section in the femoral neck. This peg has a surface, which is provided with a three-dimensional, open-mesh spatial network structure, in which and through which bone trabeculae of the surrounding bone material grow and provide for the stable secondary fixation.

There are, however, indications, in which one can still refrain from milling the femoral neck in order to create space for the peg. Here, the so-called Legg-Calve-Perthes disease is to be mentioned, which causes aseptic bone necrosis on one or both sides in the region of the femur head epiphysis. This disease appears primarily in boys of ages from 4 to 12 years old (Pschyrembel, *Klinisches Wörterbuch [Clinical Dictionary]*, 259th edition, page 1285 (2002)). Healing without deformation is indeed possible, but a possible roller or mushroom shape of the femur head with flattening of the acetabulum, more rarely coxa plana or arthrosis deformans, remains.

Another indication, for example, is a cyst in the hip-joint head, which leads to surface defects of the joint head.

Very generally, necrosis of the joint head can lead to surface defects, which, however, does not always justify the complete resection of the joint head and the accommodation of the patient with a short-stem endoprosthesis (European Patent EP 0 878 176).

In principle—and this has been increasingly recognized in recent times—it is favorable to hold off (partial) resections of bones as long as possible, in order to be able to revert back to several steps of the endoprosthetic accommodation, if a revision surgery from the short-stem endoprosthesis to the classic long-stem endoprosthesis is needed at a later time. The use of the latter endoprosthesis requires the complete resection of the femoral neck.

With a resurfacing hip implant according to German Patent DE 10 2005 011 361, a proposal has been made, which enables the greatest possible flexibility with respect to long-term preservation of the implant in situ, that is, it helps to delay an extensive endoprosthetic accommodation.

This has been realized by a set for creating a resurfacing hip implant, which has a 1 to 1.5 mm thick metallic shell for cemented insertion into the natural acetabulum, from which only cartilage has been removed, as well as a 1 to 1.5 mm thick metallic cap for cemented placement on the natural hip-joint head, from which only cartilage has been removed, and in addition an inlay having a material thickness between 2 to 5 mm, which can be inserted into the acetabulum shell as a sliding partner for the hip-joint head cap.

Both the osseous acetabulum and also the osseous hip-joint head are here processed with a profile cutter, as is the case for implanting a total hip-joint replacement implant. The acetabulum and joint head are merely freed from cartilage and connective tissue, i.e., cartilage is removed.

This implant has proven itself in practice. However, there are indications, in which defective positions in the head must be compensated. This can be the case after a trauma or else due to advanced wear.

BRIEF SUMMARY OF THE INVENTION

An object of the present invention is now to improve the set mentioned above for creating a resurfacing hip-joint implant, in such a way that defective positions of the hip-joint head can be compensated.

This object is achieved by a set for creating an offset-resurfacing hip-joint implant, which—like the set mentioned above—has a 1 to 1.5 mm thick metallic shell for insertion into the natural acetabulum, from which only cartilage has been removed. Likewise, a metallic cap for placement on the natural hip-joint head, from which only cartilage has been removed, is also part of the set. However, its wall in the region of the base edge increases constantly viewed in cross section from a thickness of 2 mm to 6 mm, so that an eccentricity arises in its outer shape. As already present in the known set, an inlay having a material thickness between 2 to 5 mm and insertable into the acetabulum shell as a sliding partner for the hip-joint head cap is also a component of the set.

With a "test cap," which has the same outer contours as the actual cap implant, the surgeon can determine the position of the metallic cap to be set on the hip-joint head by rotating it on the hip-joint head. Due to the eccentricity of the outer shape of the cap, the surgeon can simulate a compensation of the hip-joint head defective position with the "test cap." The metallic implant is then brought into the same position found to be optimal as the "test cap."

The metallic cap can be cemented on the hip-joint head. A cap to be implanted without cement, however, is also conceivable.

According to one advantageous embodiment, a guiding pin, which can be set in a borehole to be formed in the hip-joint head, is provided proximally and in the exact center of the pole region of the cap.

To permanently form the compensation of the hip-joint head defective position, at least two anti-rotation elements are advantageously provided that project into the interior of the hip-joint head cap. Then, after implantation, they engage in the bone of the hip-joint head and thus prevent rotation of the cap on the joint head. The corresponding "test cap" obviously has no anti-rotation elements, because it must be able to rotate on the joint head to find the optimal position.

According to an actual embodiment, the anti-rotation elements have a shield-shaped construction. Alternatively, they can also have a pin-shaped construction.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
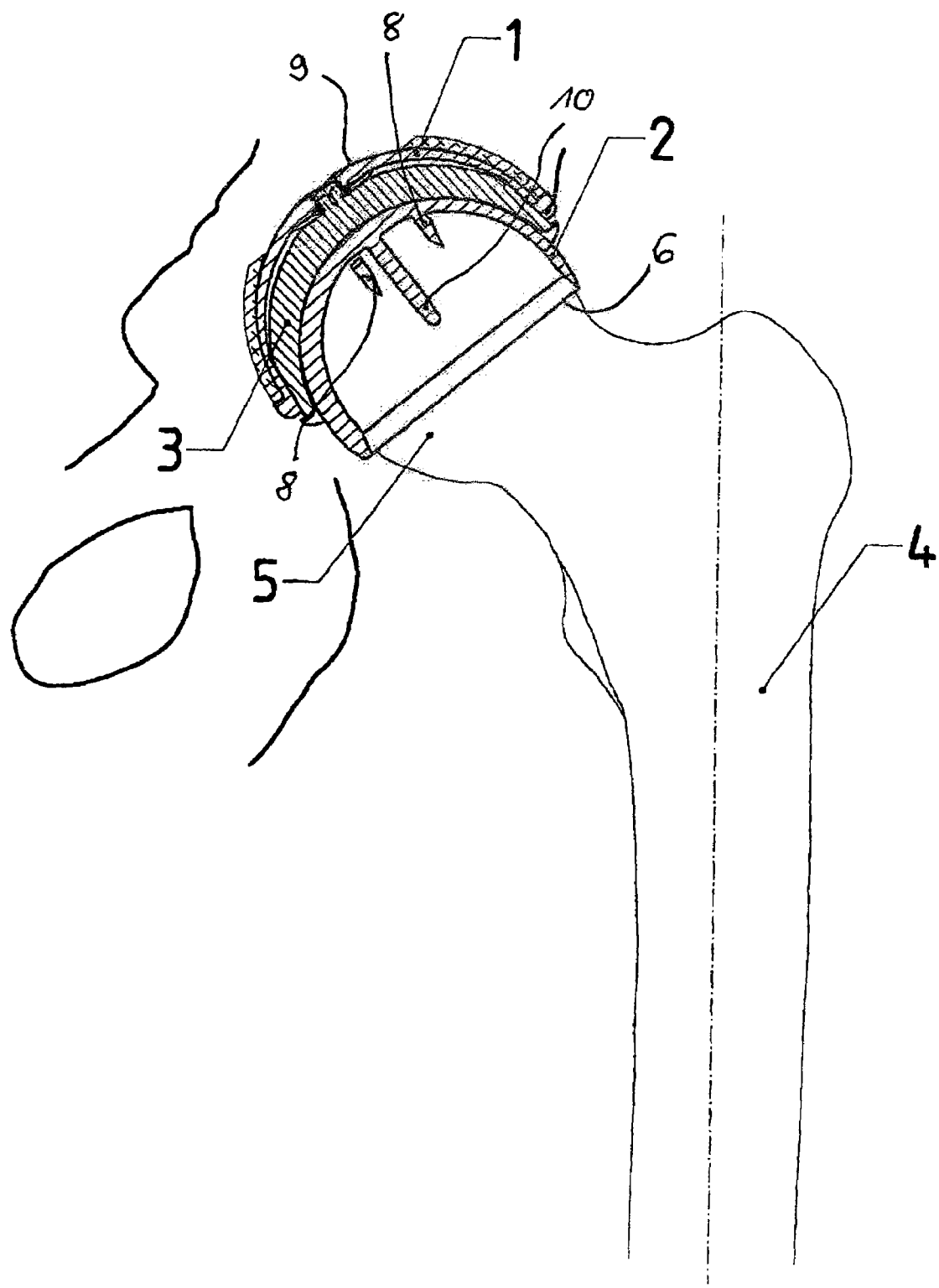
FIG. 1 is a schematic, sectional side view of a hip-joint implant assembled from a set according to an embodiment of the present invention with the shell fixed in the acetabulum and with the cap placed on the joint head.
Figure 2:
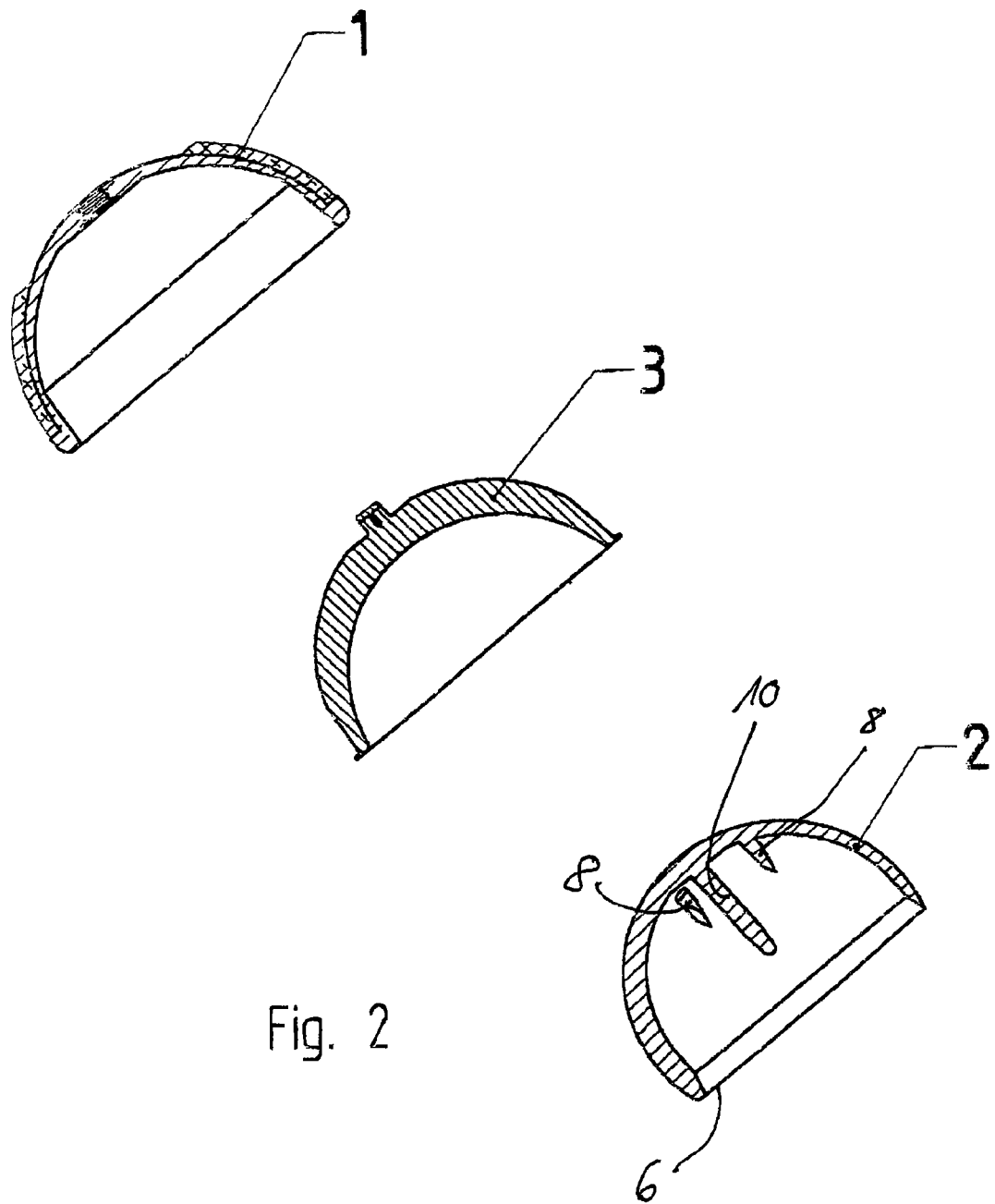
FIG. 2 is a schematic, sectional side view of the individual parts of the set according to an embodiment of the invention.

FIG. 1 illustrates schematically how the hip-joint implant, which has been created from a set according to an embodiment of the invention, is implanted. The metallic cap 2 is set on the hip-joint head 5 on the femur 4. The cap can be fixed there by a thin cement film in the interior of the cap.

The metallic shell 1 is set in the natural acetabulum 9 and fixed there with a thin cement film. The cement that is used has a very low viscosity.

The inlay 3, which forms the sliding partner for the metallic cap 2, is set in the shell 1. In the interior of the hip-joint head cap 2, a guiding peg 10, which engages in a borehole to be formed in the femoral neck 5, is formed proximally and in the exact center in the pole region. In addition, in the interior of the hip-joint head cap 2, at least two anti-rotation elements 8 project into the cap interior. The anti-rotation elements ensure that the position of the cap 2 set once on the joint head 5 is maintained stably over a long time.

Figure 3:
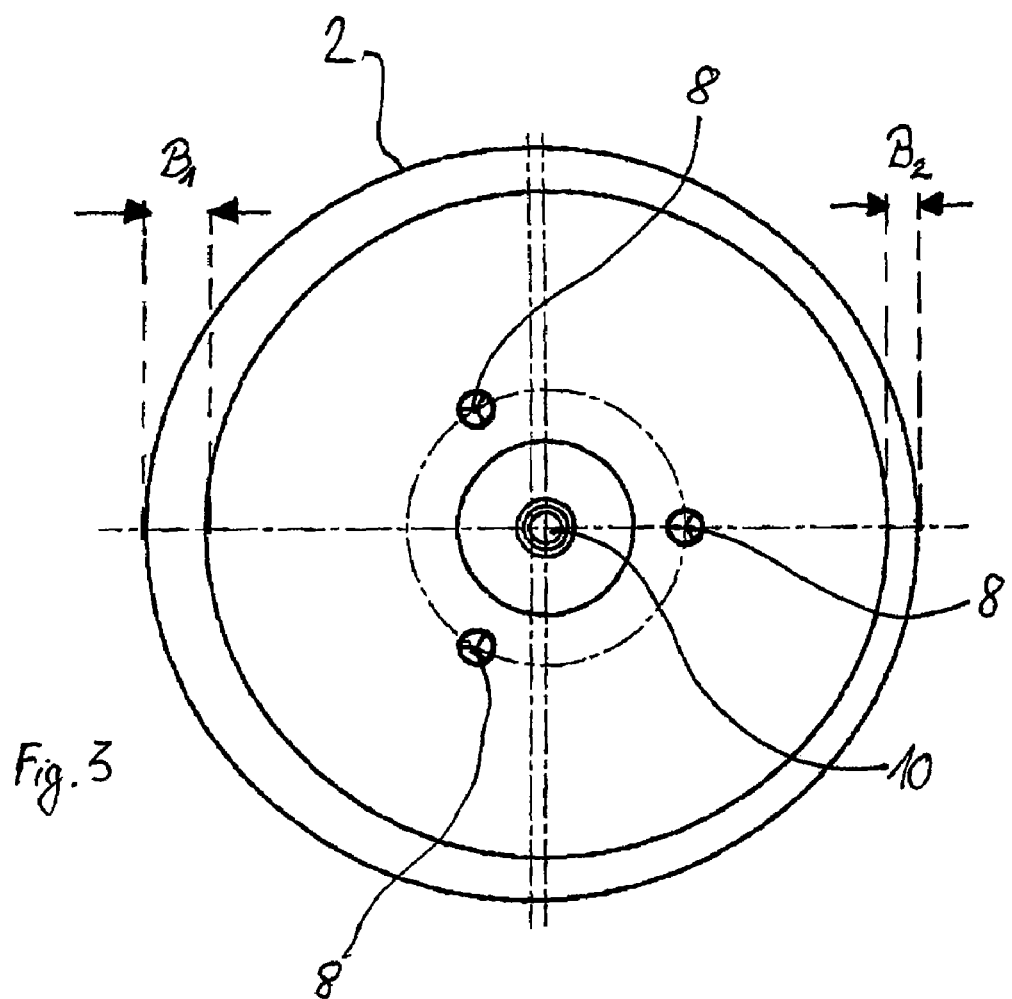
FIG. 3 is a schematic, bottom view into the interior of the cap of an embodiment of the invention.
Figure 4:
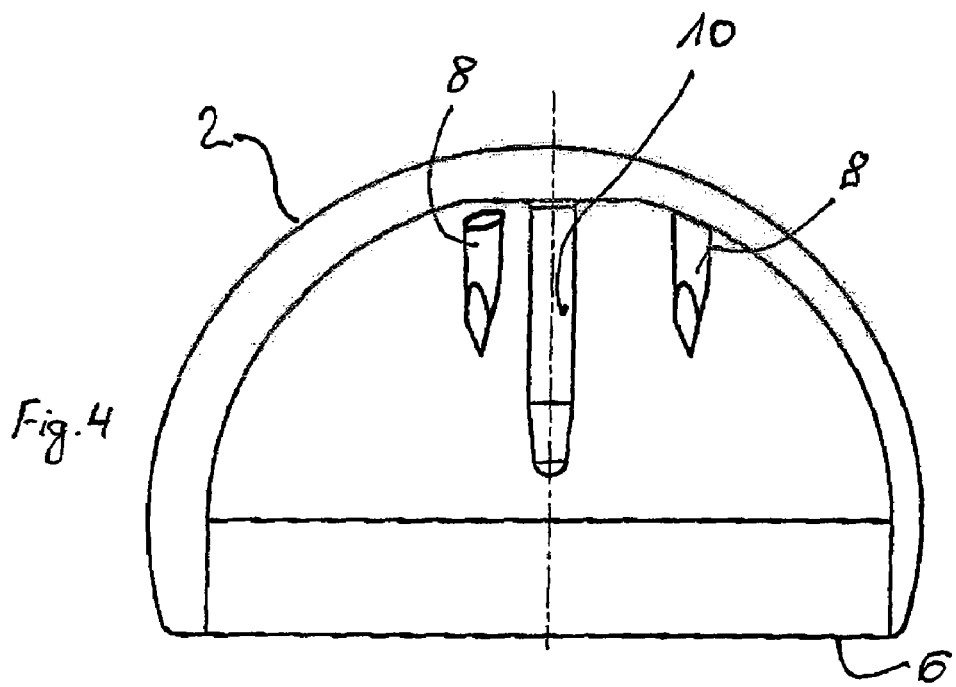
FIG. 4 is a schematic, sectional side view through the cap of the set according to an embodiment of the invention.

The special feature of the cap 2 is now that its wall thickness increases constantly viewed in cross section in the region of the base edge 6. In the illustrated embodiment, the wall thickness of the cap 2 is larger on the left than on the right. This is even clearer with reference to FIGS. 3 and 4. There it can be clearly seen that the wall is significantly wider on the left with the width $B_1$ than on the opposite side, wherein the wall has a width $B_2$. Due to this special feature, an eccentricity of the outer contours of the cap 2 is produced. With the help of this eccentricity, it is possible to compensate defective positions of the hip-joint head 5. By rotating a "test cap," which has the same outer contours as the actual implant, but which at least has no anti-rotation elements, the optimal position of the later implant can be determined in situ. The wall thickness of the cap 2 can increase constantly from 2 mm to 6 mm.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A set for creating an offset-resurfacing hip-joint implant, the set comprising a 1 to 1.5 mm thick metallic acetabulum shell (1) shaped for insertion into a natural acetabulum, from which acetabulum only cartilage has been removed, a metallic hip-joint head cap (2) shaped for placement on a natural hip-joint head, from which head only cartilage has been removed, wherein the head cap (2) has a wall which increases constantly from a thickness of 2 mm to 6 mm viewed in cross section in a region of a base edge (6) of the head cap, such that an eccentricity is produced in an outer shape of the head cap, and an inlay (3) shaped for insertion into the acetabulum shell (1) as a sliding partner for the head cap (2), the inlay having a material thickness of 2 to 5 mm.

2. The set according to claim 1, further comprising a guiding peg (10) connected to the head cap proximally and in an exact center in a pole region of the head cap (2).

3. The set according to claim 1, further comprising at least two anti-rotation elements (8) projecting into an interior of the head cap (2).

4. The set according to claim 3, wherein the anti-rotation elements (8) have a pin-shaped construction.

5. The set according to claim 2, further comprising at least two anti-rotation elements (8) projecting into an interior of the head cap (2).

6. The set according to claim 5, wherein the anti-rotation elements (8) have a pin-shaped construction.

* * * * *